United States Patent [19]

Ushikubo et al.

[11] Patent Number: 5,281,745
[45] Date of Patent: Jan. 25, 1994

[54] PROCESS FOR PRODUCING NITRILES

[75] Inventors: Takashi Ushikubo, Yokohama; Kazunori Oshima, Tokyo; Atsushi Kayo, Kurashiki; Tiaki Umezawa, Yokkaichi; Ken-ichi Kiyono, Tokyo; Itaru Sawaki, Yokkaichi, all of Japan

[73] Assignee: Mitsubishi Kasei Corporation, Tokyo, Japan

[21] Appl. No.: 926,173

[22] Filed: Aug. 7, 1992

[30] Foreign Application Priority Data

Aug. 8, 1991 [JP] Japan .................................. 3-199573
Feb. 4, 1992 [JP] Japan .................................. 4-018962

[51] Int. Cl.⁵ .......................................... C07C 353/24
[52] U.S. Cl. .................................................. 558/319
[58] Field of Search .................................... 558/319

[56] References Cited

U.S. PATENT DOCUMENTS 5,008,427  4/1991  Brazdil, Jr. et al. ............... 558/319
5,049,692  9/1991  Masakatsu et al. ............... 558/319

FOREIGN PATENT DOCUMENTS 0318295   5/1989   European Pat. Off.
0512846  11/1992   European Pat. Off.
2173203  10/1973   France
2-257     1/1990   Japan
1377325  12/1974   United Kingdom
2090156   7/1982   United Kingdom

*Primary Examiner*—Joseph Paul Brust
*Attorney, Agent, or Firm*—Oblon, Spivak, McClelland, Maier & Neustadt

[57] ABSTRACT

A process for producing a nitrile, which comprises subjecting an alkane and ammonia in the gaseous state to catalytic oxidation in the presence of a catalyst which satisfies the following conditions of (1) and (2):

(1) the catalyst is represented by the empirical formula:

$$Mo_a V_b Te_c X_x O_n \qquad (1)$$

wherein X is at least one element selected from the group consisting of Nb, Ta, W, Ti, Al, Zr, Cr, Mn, Fe, Ru, Co, Rh, Ni, Pd, Pt, Sb, Bi, B and Ce, when $a = 1$,
$b = 0.01$ to $1.0$,
$c = 0.01$ to $1.0$,
$x = 0.01$ to $1.0$.

and n is a number such that the total valency of the metal elements is satisfied; and (2) the catalyst has X-ray diffraction peaks at the following angles of $2\theta$ in its X-ray diffraction pattern:

| Diffraction angles of $2\theta$ (°) |
|---|
| $22.1 \pm 0.3$ |
| $28.2 \pm 0.3$ |
| $36.2 \pm 0.3$ |
| $45.2 \pm 0.3$ |
| $50.0 \pm 0.3$ |

12 Claims, 2 Drawing Sheets

PROCESS FOR PRODUCING NITRILES

The present invention relates to a process for producing nitriles. More particularly, it relates to an improved method for producing nitriles by using alkanes as starting material.

Nitriles such as acrylonitrile and methacrylonitrile have been industrially produced as important intermediates for the preparation of fibers, synthetic resins, synthetic rubbers and the like. The most popular method for producing such nitriles is to subject an olefin such as propylene or isobutene to a catalytic reaction with ammonia and oxygen in the presence of a catalyst in a gaseous phase at a high temperature.

For example, there have been reports on a Mo-Bi-P-O catalyst (Japanese Unexamined Patent Publication No. 16887/1973), a V-Sb-O catalyst (Japanese Unexamined Patent Publication No. 33783/1972, Japanese Examined Patent Publication No. 23016/1975 and Japanese Unexamined Patent Publication No. 268668/1989), a Sb-U-V-Ni-O catalyst (Japanese Examined Patent Publication No. 14371/1972), a Sb-Sn-O catalyst (Japanese Examined Patent Publication No. 28940/1975), a V-Sb-W-P-O catalyst (Japanese Unexamined Patent Publication No. 95439/1990), a catalyst obtained by mechanically mixing a V-Sb-W-O oxide and a Bi-Ce-Mo-W-O oxide (Japanese Unexamined Patent Publication No. 38051/1989). Further, the present inventors have reported on a Mo-V-Te-Nb-O catalyst (Japanese Unexamined Patent Publication No. 257/1990 and U.S. Pat. No. 5,049,692).

On the other hand, in view of the price difference between propane and propylene or between isobutane and isobutene, an attention has been drawn to developing a method for producing acrylonitrile or methacrylonitrile by a so-called ammooxidation reaction method wherein a lower alkane such as propane or isobutane is used as starting material, and it is catalytically reacted with ammonia and oxygen in a gaseous phase in the presence of a catalyst.

However, none of these methods is fully satisfactory in the yield of the intended nitriles. In order to improve the yield of nitriles, it has been proposed to add a small amount of an organic halide, an inorganic halide or a sulfur compound, or to add water to the reaction system. However, the former three methods have a problem of possible corrosion of the reaction apparatus, while the latter water-adding method has a problem of formation of by-products by side reactions or a problem of their treatment. Thus, each method has a practical problem for industrial application.

Further, methods using the conventional catalysts other than the Mo-V-Te-Nb-O catalyst reported by the present inventors, usually require a very high reaction temperature at a level of 500° C. or higher. Therefore, such methods are disadvantageous in terms of reactor material, production cost, etc.

The present inventors have conducted extensive researches on the method for producing a nitrile by using an alkane as starting material. As a result, they have found it possible to produce a desired nitrile in remarkably better yield than conventional methods at a relatively low temperature of a level of from 400° to 450° C. without adding a halide or water to the reaction system, by subjecting the alkane and ammonia in the gaseous state to catalytic oxidation in the presence of a catalyst comprising molybdenum (Mo), vanadium (V), tellurium (Te) and certain types of metals and having a certain specific crystal structure. The present invention have been accomplished on the basis of this discovery.

Thus, the present invention provides a process for producing a nitrile, which comprises subjecting an alkane and ammonia in the gaseous state to catalytic oxidation in the presence of a catalyst which satisfies the following conditions ① and ②:

(1) the catalyst is represented by the empirical formula:

$$Mo_a V_b Te_c X_x O_n \qquad (1)$$

wherein X is at least one element selected from the group consisting of Nb, Ta, W, Ti, Al, Zr, Cr, Mn, Fe, Ru, Co, Rh, Ni, Pd, Pt, Sb, Bi, B and Ce, when a = 1,
b = 0.01 to 1.0,
c = 0.01 to 1.0,
x = 0.01 to 1.0, and n is a number such that the total valency of the metal elements is satisfied; and (2) the catalyst has X-ray diffraction peaks at the following angles of $2\theta$ in its X-ray diffraction pattern:

| Diffraction angles of $2\theta$ (°) |
| --- |
| 22.1 ± 0.3 |
| 28.2 ± 0.3 |
| 36.2 ± 0.3 |
| 45.2 ± 0.3 |
| 50.0 ± 0.3 |

Now, the present invention will be described in detail with reference to the preferred embodiments.

The catalyst useful for the process of the present invention for producing a nitrile by reacting an alkane with ammonia by a gas phase catalytic oxidation reaction, has the above mentioned chracteristics ① and ②.

The complex oxide having such a specific crystal structure can be prepared by the following method.

For example, in the case of $Mo_a V_b Te_c Nb_x O_n$, added sequentially to an aqueous solution containing a predetermined amount of ammonium metavanadate, are an aqueous solution of telluric acid, an aqueous solution of ammonium niobium oxalate and an aqueous solution of ammonium paramolybdate in such amounts that the atomic ratios of the respective metal elements would fall in the specified ranges. Then, the mixture is dried by evaporation to dryness, a spray drying method or a vacuum drying method, and finally, the dried product is calcined to obtain the desired oxide. To efficiently conduct the calcination, the above dried product may be decomposed under heating at a temperature of from 150° to 350° C. in air or in an inert gas atmosphere such as nitrogen or argon, prior to the final calcination.

In the process for preparing the specific complex oxide to be used as the catalyst of the present invention, the calcination conditions are particularly important. For calcination treatment to prepare an ordinally oxide, it is most common to employ a method wherein calcination is conducted in an oxygen atmosphere. However, in the present invention, calcination is preferably conducted in an atmosphere substantially free from oxygen, for example, in an inert gas atmosphere such as nitrogen, argon or helium. Further, such a gas may contain a reducing gas such as hydrogen or a hydrocarbon, or steam. Otherwise, the calcination may be conducted under vacuum usually at a temperature of from 350° to 700° C., preferably from 400° to 650° C., usually for from 0.5 to 35 hours, preferably from 1 to 10 hours. At a temperature lower than this temperature range, formation of the above crystal structure presenting the high catalytic activities tends to be inadequate. On the other hand, if it exceeds the above temperature range, a part of the crystal structure is likely to be thermally decomposed, such being undesirable.

When the content of oxygen in the complex oxide thus obtained, is examined, for example, in the case of $Mo_aV_bTe_cNb_xO_n$, the value of n is smaller than $(3a+2.5b+3c+2.5x)$ which represents the value corresponding to the most highly oxidized state of Mo, V, Te and Nb, and it is at a level of from 80 to 97% thereof. Namely, the complex oxide having the specific structure to be used as the catalyst of the present invention corresponds to a complex oxide obtainable by calcining a dried product of the same starting materials under a usual oxidizing atmosphere except that the oxygen content is slightly smaller.

The catalyst of the present invention is a complex oxide of the above formula (1), wherein X is at least one element selected from the group as defined above. However, X is preferably Nb, Ta, W or Ti, particularly preferably Nb. Further, with respect to the coefficients in the formula (1), it is particularly preferred that when $a=1$, $b=0.1$ to 0.6, $c=0.05$ to 0.4, and $x=0.01$ to 0.6.

However, the complex oxide is not adequate as a catalyst for the reaction of the present invention if it merely satisfies the composition represented by the formula (1), and it is important that the complex oxide has a certain specific crystal structure.

An index showing that the complex oxide to be used as a catalyst of the present invention has the specific crystal structure, is the powder X-ray diffraction pattern. The X-ray diffraction pattern of the complex oxide is characterized in that it shows the following five main diffraction peaks at the specific diffraction angles of $2\theta$ (as measured by using Cu-Kα-rays as the X-ray source):

| Diffraction angles of $2\theta$ (°) | Center values of X-ray lattice spacing (Å) | Relative intensity |
|---|---|---|
| 22.1 ± 0.3 | 4.02 | 100 |
| 28.2 ± 0.3 | 3.16 | 20 to 150 |
| 36.2 ± 0.3 | 2.48 | 5 to 60 |
| 45.2 ± 0.3 | 2.00 | 2 to 40 |
| 50.0 ± 0.3 | 1.82 | 2 to 40 |

The intensities of X-ray diffraction peaks may differ depending upon the measuring conditions for each crystal. However, the relative intensities based on the peak intensity at $2\theta=22.1°$ being 100, are usually within the above identified ranges. In general, the peak intensities at $2\theta=22.1°$ and 28.2° are higher than others. However, so long as the above identified five diffraction peaks are observed, there will be no change in the basic crystal structure even if there are some peaks observed in addition to the above five diffraction peaks, and such a complex oxide can be suitably used for the present invention.

Thus, it is totally unexpected and surprising that the complex oxide not only has the specific crystal structure but also provides remarkably high catalytic activities as compared with the conventional catalyst in the reaction to obtain a nitrile from an alkane as starting material.

Further, the materials for the above complex oxide are not limited to the ones described above. For example, $V_2O_5$, $V_2O_3$, $VOCl_3$ or $VCl_4$ may be used instead of ammonium metavanadate, and $TeO_2$ may be used instead of telluric acid. Likewise, $NbCl_5$, $Nb_2O_5$ or niobic acid may be used instead of ammonium niobium oxalate, and $MoO_3$ or $MoCl_5$ may be used instead of ammonium paramolybdate.

The complex oxide of the formula (1) prepared in the manner as described above, has adequate catalytic activities by itself. However, in order to further improve the selectivity and yield of the nitrile, it is particularly preferred to use a catalyst having a certain specific oxide incorporated to the complex oxide. As such a specific oxide, it is possible to employ an oxide containing at least one member selected from the group consisting of antimony, bismuth, cerium and boron. An antimony oxide is particularly preferred.

The antimony oxide to be incorporated may, for example, be an antimony oxide such as $Sb_2O_3$, $Sb_2O_4$ or $Sb_2O_5$, and it may otherwise be an oxide having a composition of e.g. $SbO_2\cdot(Sb_2O_4)$. These oxides may be used alone or in combination as a mixture of a plurality of them. Otherwise, it may be used in the form of a hydrate. Further, in some cases, it is possible to employ as a solid catalyst a substance prepared by incorporating an organic compound containing antimony, such as ammonium antimony tartarate or antimony oxalate to the complex oxide of the formula (1), followed by calcination. In this case, the organic compound containing antimony will be converted to antimony oxide by the calcination.

The bismuth oxide to be incorporated may, for example, be a bismuth oxide such as $Bi_2O_3$ or $Bi_2O_4$, and it may also be a hydrate such as $Bi_2O_4\cdot 2H_2O$. These oxides may be used alone or in combination as a mixture of a plurality of them. In some cases, a salt of an organic or inorganic acid or a hydroxide containing bismuth, such as bismuth hydroxide, bismuth nitrate, bismuth nitrate oxide or bismuth acetate may be added to the complex oxide of the formula (1), followed by calcination, and the substance thereby obtained can be used as a solid catalyst. In this case, the salt or the hydroxide containing bismuth will be converted to bismuth oxide by the calcination.

The cerium oxide may, for example, be a cerium oxide such as $Ce_2O_3$ or $CeO_2$. These oxides may be used alone or in combination as a mixture of a plurality of them. In some cases, a salt of an organic or inorganic acid, or a hydroxide containing cerium, such as cerium nitrate, cerium hydroxide, cerium oxalate or cerium acetate, may be added to the complex oxide of the formula (1), followed by calcination, and the product of the calcination can be used as a solid catalyst. In this case, the salt or the hydroxide containing cerium will be converted to cerium oxide by the calcination. The boron oxide is usually $B_2O_3$. However, a boric acid or a boric acid ester, such as orthoboric acid, metaboric acid, ethy borate or propyl borate, may be added to the complex oxide of the formula (1), followed by calcination, and the calcined product can be used as a solid catalyst. In such a case, the boric acid or the boric acid ester is believed to be converted to boron oxide by the calcination.

As a method for incorporating the above mentioned specific oxide to the complex oxide, it is advisable to pulverize and mix both materials so that the contact of the specific oxide with the complex oxide can be effectively done. The amount of the specific oxide to the complex oxide is usually from 0.0001 to 0.2, preferably from 0.001 to 0.05 by the weight ratio to the complex oxide. After the addition, the mixture may be used as it is for the reaction to produce a nitrile from an alkane. However, in order to effectively obtain the effects of the addition of the specific oxide, it is preferred to calcine the mixture again at a temperature of from 300° to 650° C., preferably from 350° to 600° C., usually for from 0.5 to 30 hours, preferably from 1 to 10 hours. The atmosphere for calcination is not particularly limited, but it is usually preferred to employ an inert gas atmosphere such as nitrogen, argon or helium, and the inert gas may further contain a reducing gas such as hydrogen, ammonia or a hydrocarbon, or steam. Otherwise, the calcination may be conducted under vacuum.

Even if the specific oxide is added to the complex oxide, followed by mixing and calcination, the X-ray diffraction pattern of the obtained product is substantially the same as that of the complex oxide before the addition of the specific oxide, and there is no substantial change observed in the crystal structure.

The above catalyst may be used alone. However, it may be used together with a conventional carrier such as silica, alumina, titania, aluminosilicate or diatomaceous earth. Further, depending upon the scale or system of the reaction, it may be molded into a proper shape and particle size.

According to the present invention, a nitrile can be produced efficiently by subjecting an alkane to a gas phase catalytic oxidation reaction with ammonia in the presence of the above catalyst.

In the present invention, the alkane as the starting material is not particularly limited and may, for example, be methane, ethane, propane, butane, isobutane, pentane, hexane, heptane. However, in view of the industrial application of nitriles to be produced, it is particularly preferred to employ a lower alkane having from 1 to 4 carbon atoms, particularly propane or isobutane.

The detailed mechanism of the oxidation reaction of the present invention is not clearly understood. However, the oxidation reaction is conducted by the oxygen atoms present in the above complex oxide or by the molecular oxygen present in the feed gas. When molecular oxygen is incorporated in the feed gas, the oxygen may be pure oxygen gas. However, since the purity is not required, it is usually economical to use an oxygen-containing gas such as air.

As the feed gas, it is common to use a gas mixture comprising an alkane, ammonia and an oxygen-containing gas. However, a gas mixture comprising an alkane and ammonia, and an oxygen-containing gas may be supplied alternately.

When the gas phase catalytic reaction is conducted using an alkane and ammonia substantially free from molecular oxygen, as the feed gas, it is advisable to employ a method wherein a part of the catalyst is properly withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° to 600° C.

The present invention will be described in further detail with respect to a case where propane is used as the alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 mols, particularly from 1 to 15 mols, per mol of propane. The proportion of ammonia to be supplied for the reaction is preferably within a range of from 0.2 to 5 mols, particularly from 0.5 to 3 mols, per mol of propane. This reaction may usually be conducted under atmospheric pressure, but may be conducted under a slightly increased pressure or a slightly reduced pressure. With respect to other alkanes, the composition of the feed gas can be selected in accordance with the conditions for propane.

The process of the present invention can be conducted at a temperature of e.g. from 340° to 480° C., which is lower than the temperature for conventional ammooxidation of alkanes. More preferably, the temperature is from 400° to 450° C. The gas space velocity SV in the gas phase reaction is usually within a range of from 100 to 10,000 $hr^{-1}$, preferably from 300 to 2,000 $hr^{-1}$. As a diluent gas for adjusting the space velocity and the oxygen partial pressure, an inert gas such as nitrogen, argon or helium can be employed. When ammooxidation of propane is conducted by the method of the present invention, in addition to acrylonitrile, carbon monooxide, carbon dioxide, acetonitrile, hydrocyanic acid, acrolein, etc. will form as by-products, but their amounts are very small.

Now, the present invention will be described in further detail with reference to Examples and Comparative Examples. However, it should be understood that the present invention is by no means restricted to such specific Examples.

In the following Examples and Comparative Examples, the conversion (%), the selectivity (%) and the yield (%) are shown by the following formulas, respectively:

$$\text{Conversion of alkane (\%)} = \frac{\text{mols of consumed alkane}}{\text{mols of supplied alkane}} \times 100$$

$$\text{Selectivity of objective nitrile (\%)} = \frac{\text{mols of objective nitrile obtained}}{\text{mols of consumed alkane}} \times 100$$

$$\text{Yield of objective nitrile (\%)} = \frac{\text{mols of supplied alkane}}{\text{mols of objective nitrile obtained}} \times 100$$

EXAMPLE 1

A complex oxide having an empirical formula $Mo_1V_{0.4}Te_{0.2}Nb_{0.1}O_n$ was prepared as follows.

In 117 ml of warm water, 4.21 g of ammonium metavanadate was dissolved, and 4.13 g of telluric acid and 15.89 g of ammonium paramolybdate were sequentially added thereto to obtain a uniform aqueous solution.

Further, 3.99 g of ammonium niobium oxalate was dissolved in 17.9 ml of water and added thereto to obtain a slurry. The obtained slurry was evaporated to dryness at about 150° C. to obtain a dried product.

Figure 1:
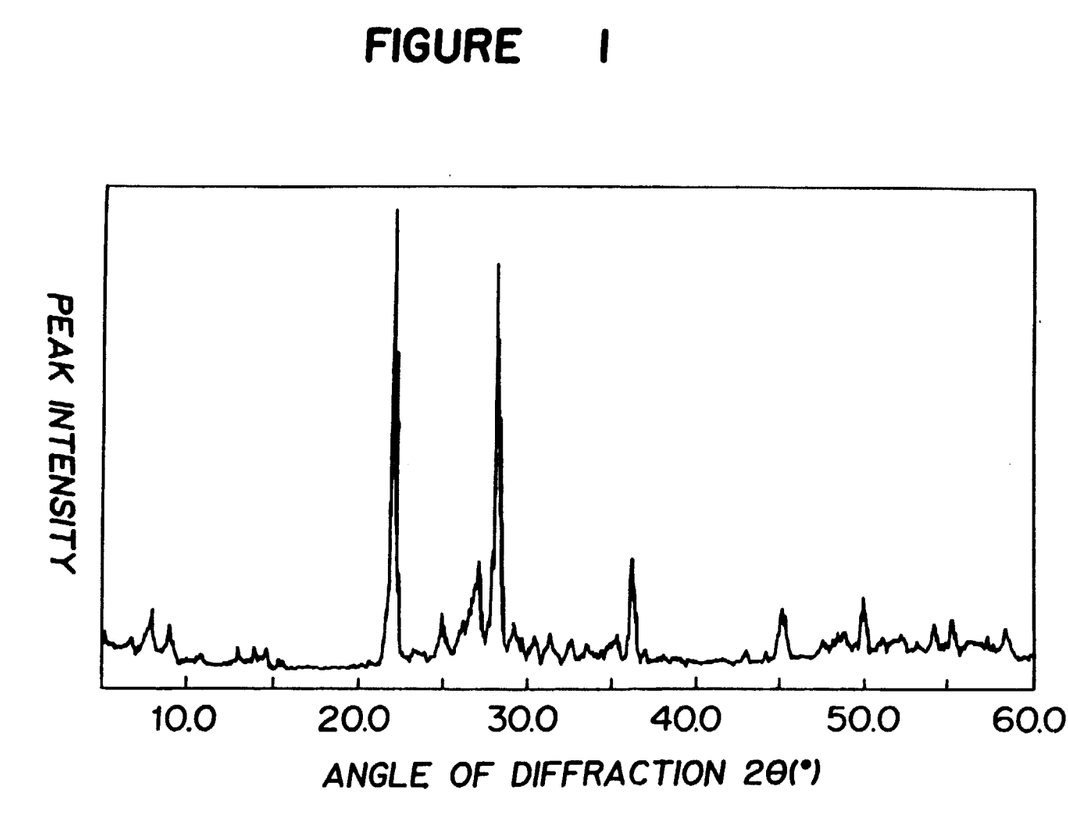
FIG. 1 shows the powder X-ray diffraction pattern of the complex oxide obtained in Example 1.

This dried product was molded into a tablet of 5 mm in diameter and 3 mm in length by a tabletting machine, followed by pulverization and sieving to obtain a powder of from 16 to 28 mesh. The powder was calcined in a nitrogen stream at a temperature of 620° C. for two hours. FIG. 1 shows a chart of the peaks of the powder X-ray diffraction pattern of the complex oxide thus obtained, and Table 1 shows the relative intensities of the main X-ray diffraction peaks.

Further, the oxygen content in the complex oxide was measured by an oxygen analyzer and was found to be 31.0% by weight. From this measured value, the coefficient n for O (oxygen) was calculated to be 4.25. The value $n=4.25$ corresponds to 87.6% of $n=4.85$ which is the most highly oxidized state of the constituting elements of the complex oxide where Mo is hexavalent, V is pentavalent, Te is hexavalent and Nb is pentavalent.

0.5 ml of the catalyst thus obtained, was charged into a reactor. Then, a gas phase catalytic reaction was conducted at a reaction temperature of 440° C. and at a space velocity SV of 1,000 $hr^{-1}$ by supplying a feed gas in a molar ratio of propane:ammonia:air = 1:1.2:10. The results are shown in Table 2.

EXAMPLES 2 AND 3

Complex oxides having an empirical formula $Mo_1V_{0.4}Te_{0.2}Nb_{0.1}O_n$ were prepared in the same manner as in Example 1 except that the temperature for calcination in Example 1 was changed to 500° C. and 600° C.

The results of the powder X-ray diffraction of the complex oxides are shown in Table 1. Further, the results of the gas phase catalytic reactions are shown in Table 2.

COMPARATIVE EXAMPLE 1

A complex oxide having an empirical formula $Mo_1V_{0.4}Te_{0.2}O_n$ was prepared in the same manner as in Example 2 except that the niobium component in Example 2 was not used.

The X-ray diffraction pattern of the complex oxide was totally different from that of Example 1. The results of the gas phase catalytic reaction are shown in Table 2.

COMPARATIVE EXAMPLE 2

Figure 2:
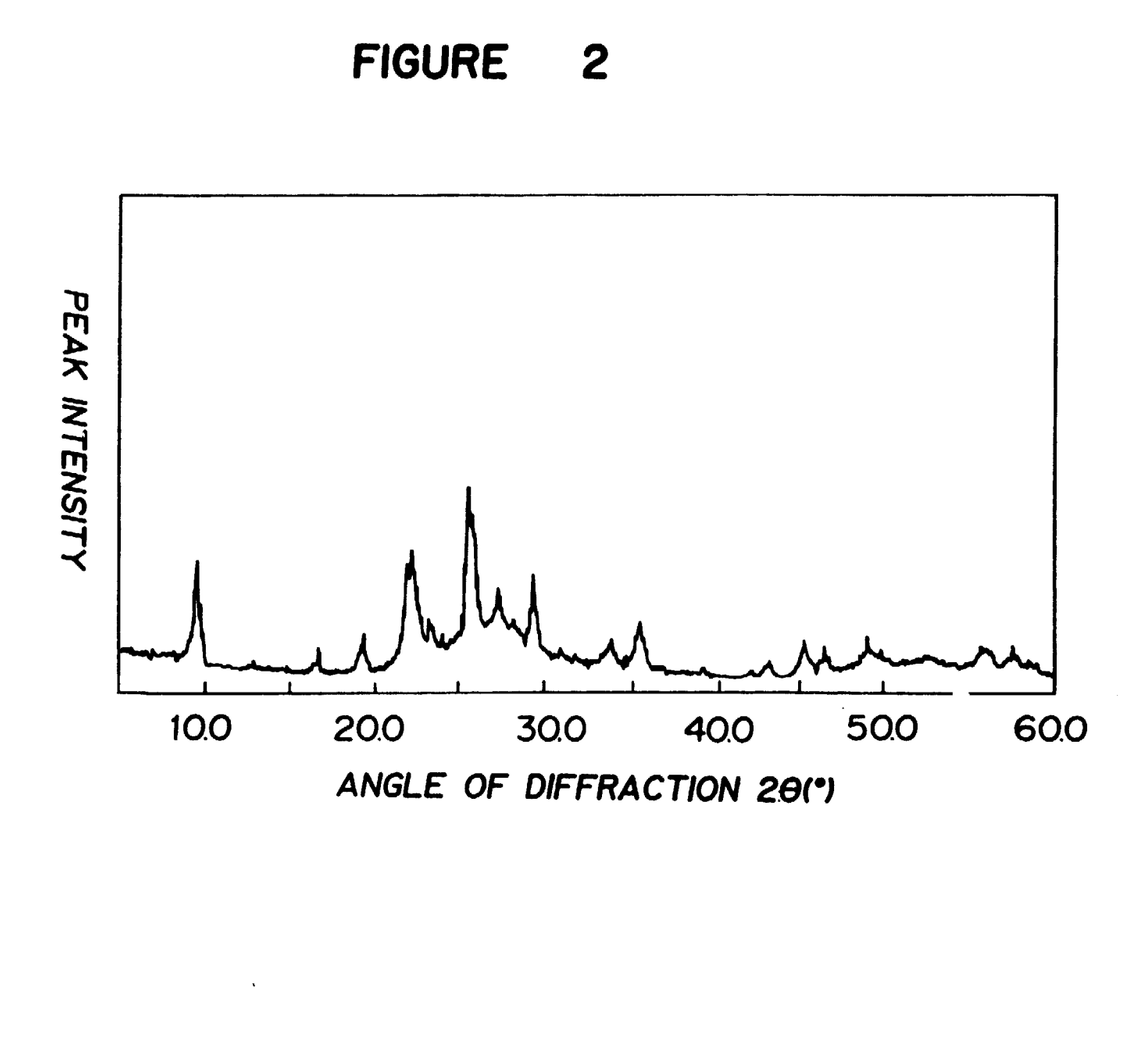
FIG. 2 shows the powder X-ray diffraction pattern of the complex oxide obtained in Comparative Example 2.

A complex oxide having an empirical formula $Mo_1V_{0.4}Te_{0.2}Nb_{0.1}O_n$ was prepared in the same manner as in Example 1 except that calcination in Example 1 was conducted under an air stream at 350° C. for two hours. The powder X-ray diffraction pattern of the complex oxide thus obtained, is shown in FIG. 2. The pattern is entirely different from the pattern in FIG. 1 representing Example 1.

Further, the results of the gas phase catalytic reaction are shown in Table 2.

COMPARATIVE EXAMPLES 3 AND 4

Using the complex oxide of Comparative Example 2, the gas phase catalytic reaction was conducted under the reaction conditions as identified in Table 2. The results are shown in Table 2.

EXAMPLE 4

A complex oxide having an empirical formula $Mo_1V_{0.4}Te_{0.2}Sb_{0.1}O_n$ was prepared as follows.

In 117 ml of warm water, 4.21 g of ammonium metavanadate was dissolved, and 4.13 g of telluric acid and 15.9 g of ammonium paramolybdate were sequentially added thereto to obtain a uniform aqueous solution. Further, 1.56 g of antimony chloride oxide was dissolved in 17.9 ml of water and mixed thereto. The obtained aqueous solution was evaporated to dryness to obtain a dried product.

This dried product was molded into a tablet of 5 mm in diameter and 3 mm in length by a tabletting machine, followed by pulverization and sieving to obtain a powder of from 16 to 28 mesh. The powder was calcined in a nitrogen stream at 500° C. for two hours. The results of the powder X-ray diffraction of the complex oxide thus obtained are shown in Table 1.

With respect to the complex oxide thus obtained, the gas phase catalytic reaction was conducted, and the results are shown in Table 2.

COMPARATIVE EXAMPLE 4

A complex oxide having an empirical formula $Mo_1V_{0.4}Te_{0.2}Sb_{0.1}O_n$ was prepared in the same manner as in Example 4 except that the calcination in Example 4 was conducted under an air stream at 350° C. for two hours. The X-ray diffraction pattern of the complex oxide thus obtained, was entirely different from that of Example 4. Further, using the complex oxide thus obtained, a gas phase catalytic reaction as conducted, and the results are shown in Table 2.

EXAMPLE 5

A complex oxide was prepared in the same manner as in Example 4 except that 3.38 g of aluminum nitrate nonahydrate was used instead of antimony chloride oxide in Example 4. The empirical formula of the complex oxide thus obtained, was $Mo_1V_{0.4}Te_{0.2}Al_{0.1}O_n$. The results of the powder X-ray diffraction of the complex oxide thus obtained are shown in Table 1. Further, using the oxide thus obtained, a gas phase catalytic reaction was conducted, and the results are shown in Table 2.

COMPARATIVE EXAMPLE 5

A complex oxide having an empirical formula $Mo_1V_{0.4}Te_{0.2}Al_{0.1}O_n$ was prepared in the same manner as in Example 5 except that the calcination in Example 5 was conducted under an air stream at 350° C. for two hours. The X-ray diffraction pattern of the complex oxide thus obtained, was entirely different from that of Example 5. Further, using the complex oxide thus obtained, a gas phase catalytic reaction was conducted, and the results are shown in Table 2.

EXAMPLE 6

A complex oxide was prepared in the same manner as in Example 4 except that 0.415 g of palladium nitrate was used instead of antimony chloride oxide in Example 4 and the temperature for calcination was changed to 600° C. The empirical formula of the complex oxide thus obtained, was $Mo_1V_{0.4}Te_{0.2}Nb_{0.1}Pd_{0.02}O_n$. The results of the powder X-ray diffraction of the complex oxide thus obtained, are shown in Table 1. Further, using the complex oxide thus obtained, a gas phase catalytic reaction was conducted, and the results are shown in Table 2.

EXAMPLES 7 to 23

Complex oxides having the respective empirical formulas as identified in Table 1, were prepared in the same manner as in Example 1 except that the proportions of the starting material compounds were changed and the temperature for calcination was 600° C. in each case. The results of the powder X-ray diffraction of the respective complex oxides are shown in Table 1. Further, using the respective complex oxides, gas phase catalytic reactions were conducted, and the results are shown in Table 3.

EXAMPLES 24 TO 32

Using the complex oxide prepared in Example 3 (empirical formula $Mo_1V_{0.4}Te_{0.2}Nb_{0.1}O_n$), gas phase catalytic oxidation reactions were conducted under various conditions, and the results are shown in Table 4.

TABLE 1

| Example Nos. | Complex oxides (atomic ratios) | Relative intensities of X-ray diffraction peaks at diffraction angles of $2\theta$ ($\pm 0.3°$) | | | | |
|---|---|---|---|---|---|---|
| | | 22.1° | 28.2° | 36.2° | 45.2° | 50.0° |
| 1 | $Mo_1V_{0.4}Te_{0.2}Nb_{0.1}O_n$ | 100 | 79.5 | 21.0 | 10.9 | 12.3 |
| 2 | $Mo_1V_{0.4}Te_{0.2}Nb_{0.1}O_n$ | 100 | 92.8 | 18.7 | 11.5 | 13.2 |
| 3 | $Mo_1V_{0.4}Te_{0.2}Nb_{0.1}O_n$ | 100 | 93.0 | 24.9 | 12.9 | 14.4 |
| 4 | $Mo_1V_{0.4}Te_{0.2}Sb_{0.1}O_n$ | 100 | 122.5 | 36.1 | 12.2 | 23.0 |
| 5 | $Mo_1V_{0.4}Te_{0.2}Al_{0.1}O_n$ | 100 | 97.4 | 27.6 | 13.7 | 20.0 |
| 6 | $Mo_1V_{0.4}Te_{0.2}Nb_{0.1}Pd_{0.02}O_n$ | 100 | 80.9 | 21.8 | 11.1 | 12.6 |
| 7 | $Mo_1V_{0.3}Te_{0.2}Nb_{0.15}O_n$ | 100 | 63.6 | 17.4 | 12.4 | 11.0 |
| 8 | $Mo_1V_{0.375}Te_{0.2}Nb_{0.175}O_n$ | 100 | 87.6 | 25.1 | 15.6 | 16.9 |
| 9 | $Mo_1V_{0.35}Te_{0.2}Nb_{0.15}O_n$ | 100 | 46.5 | 12.6 | 15.0 | 7.9 |
| 10 | $Mo_1V_{0.334}Te_{0.2}Nb_{0.167}O_n$ | 100 | 63.8 | 17.6 | 13.1 | 10.9 |
| 11 | $Mo_1V_{0.25}Te_{0.2}Nb_{0.15}O_n$ | 100 | 51.7 | 13.6 | 12.8 | 8.8 |
| 12 | $Mo_1V_{0.32}Te_{0.2}Nb_{0.13}O_n$ | 100 | 67.5 | 20.2 | 13.9 | 12.3 |
| 13 | $Mo_1V_{0.34}Te_{0.2}Nb_{0.12}O_n$ | 100 | 78.9 | 22.2 | 13.8 | 15.5 |
| 14 | $Mo_1V_{0.2}Te_{0.2}Nb_{0.14}O_n$ | 100 | 54.7 | 14.9 | 13.6 | 9.3 |
| 15 | $Mo_1V_{0.56}Te_{0.2}Nb_{0.14}O_n$ | 100 | 107.7 | 27.5 | 13.7 | 21.1 |
| 16 | $Mo_1V_{0.45}Te_{0.2}Nb_{0.05}O_n$ | 100 | 113.9 | 24.7 | 11.4 | 16.5 |
| 17 | $Mo_1V_{0.3}Te_{0.2}Nb_{0.2}O_n$ | 100 | 37.0 | 9.7 | 10.7 | 5.7 |
| 18 | $Mo_1V_{0.4}Te_{0.2}Nb_{0.2}O_n$ | 100 | 69.9 | 18.2 | 10.3 | 11.2 |
| 19 | $Mo_1V_{0.3}Te_{0.2}Nb_{0.1}O_n$ | 100 | 89.9 | 26.2 | 14.7 | 16.8 |
| 20 | $Mo_1V_{0.48}Te_{0.2}Nb_{0.12}O_n$ | 100 | 104.7 | 26.2 | 13.3 | 16.1 |
| 21 | $Mo_1V_{0.28}Te_{0.2}Nb_{0.14}O_n$ | 100 | 51.5 | 14.8 | 12.2 | 8.8 |
| 22 | $Mo_1V_{0.4}Te_{0.1}Nb_{0.1}O_n$ | 100 | 67.5 | 18.0 | 18.0 | 11.5 |
| 23 | $Mo_1V_{0.4}Te_{0.3}Nb_{0.1}O_n$ | 100 | 109.3 | 29.2 | 13.2 | 17.9 |

TABLE 2

| | Complex oxides (atomic ratios) | Calcination conditions | | Reaction temp. (°C.) | Space velocity (hr$^{-1}$) | Feed gas composition (mol %) propane/ammonia/air | Conversion of propane (%) | Selectivity for acrylonitrile (%) | Yield of acrylonitrile (%) |
|---|---|---|---|---|---|---|---|---|---|
| | | Temp. (°C.) | Gas stream | | | | | | |
| Example 1 | $Mo_1V_{0.4}Te_{0.2}Nb_{0.1}O_n$ | 620 | $N_2$ | 420 | 1,000 | 1/1.2/15 | 79.4 | 63.5 | 50.4 |
| Example 2 | $Mo_1V_{0.4}Te_{0.2}Nb_{0.1}O_n$ | 500 | $N_2$ | 400 | 500 | 1/1.2/10 | 54.4 | 39.4 | 21.4 |
| Example 3 | $Mo_1V_{0.4}Te_{0.2}Nb_{0.1}O_n$ | 600 | $N_2$ | 420 | 1,000 | 1/1.2/15 | 78.3 | 61.2 | 48.0 |
| Comparative Example 1 | $Mo_1V_{0.4}Te_{0.2}O_n$ | 500 | $N_2$ | 440 | 1,000 | 1/1.2/15 | 43.4 | 36.7 | 15.9 |
| Comparative Example 2 | $Mo_1V_{0.4}Te_{0.2}Nb_{0.1}O_n$ | 350 | air | 400 | 500 | 1/1.2/10 | 42.9 | 34.4 | 14.8 |
| Comparative Example 3 | $Mo_1V_{0.4}Te_{0.2}Nb_{0.1}O_n$ | 350 | air | 420 | 500 | 1/1.2/10 | 43.2 | 27.1 | 11.7 |
| Comparative Example 4 | $Mo_1V_{0.4}Te_{0.2}Nb_{0.1}O_n$ | 350 | air | 440 | 1,000 | 1/1.2/10 | 48.8 | 34.2 | 16.7 |
| Example 4 | $Mo_1V_{0.4}Te_{0.2}Sb_{0.1}O_n$ | 500 | $N_2$ | 420 | 500 | 1/1.2/10 | 47.7 | 45.5 | 21.7 |
| Comparative Example 5 | $Mo_1V_{0.4}Te_{0.2}Sb_{0.1}O_n$ | 350 | air | 400 | 500 | 1/1.2/10 | 43.0 | 36.6 | 15.7 |
| Example 5 | $Mo_1V_{0.4}Te_{0.2}Al_{0.1}O_n$ | 500 | $N_2$ | 440 | 500 | 1/1.2/10 | 60.3 | 39.1 | 23.5 |
| Comparative Example 6 | $Mo_1V_{0.4}Te_{0.2}Al_{0.1}O_n$ | 350 | air | 420 | 500 | 1/1.2/10 | 52.7 | 33.3 | 17.5 |
| Example 6 | $Mo_1V_{0.4}Te_{0.2}Nb_{0.1}Pd_{0.02}O_n$ | 600 | $N_2$ | 420 | 1,000 | 1/1.2/15 | 79.4 | 63.5 | 50.4 |

TABLE 3

| Example Nos. | Complex oxides (atomic ratios) | Reaction temp. (°C.) | Space velocity (hr$^{-1}$) | Feed gas composition (mol %) propane/ammonia/air | Conversion of propane (%) | Selectivity for acrylonitrile (%) | Yield for acrylonitrile (%) |
|---|---|---|---|---|---|---|---|
| 7 | $Mo_1V_{0.3}Te_{0.2}Nb_{0.15}O_n$ | 420 | 1,000 | 1/1.2/15 | 89.1 | 60.0 | 53.5 |
| 8 | $Mo_1V_{0.375}Te_{0.2}Nb_{0.175}O_n$ | 420 | 1,000 | 1/1.2/15 | 88.4 | 52.8 | 46.7 |
| 9 | $Mo_1V_{0.35}Te_{0.2}Nb_{0.15}O_n$ | 410 | 1,000 | 1/1.2/15 | 86.0 | 55.3 | 47.6 |
| 10 | $Mo_1V_{0.334}Te_{0.2}Nb_{0.167}O_n$ | 430 | 1,000 | 1/1.2/15 | 90.4 | 55.9 | 50.9 |
| 11 | $Mo_1V_{0.25}Te_{0.2}Nb_{0.15}O_n$ | 400 | 1,000 | 1/1.2/15 | 75.3 | 60.2 | 45.3 |
| 12 | $Mo_1V_{0.32}Te_{0.2}Nb_{0.13}O_n$ | 420 | 1,000 | 1/1.2/15 | 92.7 | 57.5 | 53.3 |
| 13 | $Mo_1V_{0.39}Te_{0.2}Nb_{0.12}O_n$ | 420 | 1,000 | 1/1.2/15 | 91.0 | 54.5 | 49.6 |
| 14 | $Mo_1V_{0.2}Te_{0.2}Nb_{0.14}O_n$ | 400 | 1,000 | 1/1.2/15 | 60.5 | 64.0 | 38.7 |
| 15 | $Mo_1V_{0.56}Te_{0.2}Nb_{0.14}O_n$ | 430 | 1,000 | 1/1.2/15 | 50.6 | 62.3 | 31.5 |
| 16 | $Mo_1V_{0.45}Te_{0.2}Nb_{0.05}O_n$ | 430 | 1,000 | 1/1.2/15 | 52.4 | 56.3 | 29.5 |
| 17 | $Mo_1V_{0.3}Te_{0.2}Nb_{0.2}O_n$ | 440 | 1,000 | 1/1.2/15 | 77.2 | 56.2 | 43.4 |
| 18 | $Mo_1V_{0.4}Te_{0.2}Nb_{0.2}O_n$ | 430 | 1,000 | 1/1.2/15 | 79.6 | 61.7 | 49.1 |
| 19 | $Mo_1V_{0.3}Te_{0.2}Nb_{0.1}O_n$ | 420 | 1,000 | 1/1.2/15 | 83.0 | 62.1 | 51.6 |
| 20 | $Mo_1V_{0.48}Te_{0.2}Nb_{0.12}O_n$ | 430 | 1,000 | 1/1.2/15 | 75.4 | 59.3 | 44.7 |
| 21 | $Mo_1V_{0.28}Te_{0.2}Nb_{0.14}O_n$ | 410 | 1,000 | 1/1.2/15 | 82.8 | 63.3 | 52.4 |
| 22 | $Mo_1V_{0.4}Te_{0.1}Nb_{0.1}O_n$ | 430 | 500 | 1/1.2/10 | 67.7 | 56.1 | 38.0 |

TABLE 3-continued

| Example Nos. | Complex oxides (atomic ratios) | Reaction temp. (°C.) | Space velocity (hr$^{-1}$) | Feed gas composition (mol %) propane/ammonia/air | Conversion of propane (%) | Selectivity for acrylonitrile (%) | Yield for acrylonitrile (%) |
|---|---|---|---|---|---|---|---|
| 23 | $Mo_1V_{0.4}Te_{0.3}Nb_{0.1}O_n$ | 420 | 1,000 | 1/1.2/15 | 44.6 | 48.6 | 21.7 |

TABLE 4

| Example Nos. | Temp. (°C.) | Space velocity (hr$^{-1}$) | Feed gas composition (mol %) propane/ammonia/air | Conversion of propane (%) | Selectivity for acrylonitrile (%) | Yield of acrylonitrile (%) |
|---|---|---|---|---|---|---|
| 24 | 420 | 1,000 | 1/0.7/15 | 82.5 | 53.1 | 43.8 |
| 25 | 420 | 1,000 | 1/0.9/15 | 82.8 | 57.5 | 47.6 |
| 26 | 420 | 1,000 | 1/1.5/15 | 81.4 | 60.2 | 49.6 |
| 27 | 420 | 1,000 | 1/1.2/10 | 62.9 | 63.8 | 40.1 |
| 28 | 420 | 1,000 | 1/1.2/17 | 82.6 | 57.6 | 47.5 |
| 29 | 420 | 500 | 1/1.2/10 | 63.0 | 56.6 | 35.7 |
| 30 | 420 | 800 | 1/1.2/15 | 84.9 | 57.9 | 49.2 |
| 31 | 420 | 1,200 | 1/1.2/15 | 77.8 | 61.7 | 48.0 |
| 32 | 410 | 1,000 | 1/0.7/15 | 76.2 | 59.1 | 45.0 |

EXAMPLE 33

A complex oxide having an empirical formula $Mo_1V_{0.3}Te_{0.23}Nb_{0.12}O_n$ was prepared as follows.

In 325 ml of warm water, 15.7 g of ammonium metavanadate was dissolved, and 23.6 g of telluric acid and 78.9 g of ammonium paramolybdate were sequentially added thereto to obtain a uniform aqueous solution. Further, 117.5 g of an aqueous ammonium niobium oxalate solution having a niobium concentration of 0.456 mol/kg was added thereto to obtain a slurry. This slurry was evaporated to dryness to obtain a solid. This solid was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

The powder X-ray diffraction of the complex oxide thus obtained was measured (using Cu-Kα-rays), whereby main diffraction peaks were observed at diffraction angles of 2θ (°) of 22.1 (100), 28.2 (90.0), 36.2 (25.7), 45.1 (15.2) and 50.0 (16.3) (the numerical values in the blackets indicate the relative peak intensities based on the peak at 22.1° being 100).

Then, 30 g of the complex oxide was pulverized in a mortar, and 0.3 g of tetravalent antimony oxide ($Sb_2O_4$) was added and mixed thereto. This mixture was molded into a tablet of 5 mm in diameter and 3 mm in length by a tabletting machine, followed by pulverization and sieving to obtain a powder of from 16 to 28 mesh. The powder was then calcined in a nitrogen stream at 500° C. for two hours.

0.5 ml of the solid catalyst thus obtained, was charged into a reactor, and the gas phase catalytic reaction was conducted at a reaction temperature of 410° C. and at a space velocity SV of 1,000 hr$^{-1}$ by supplying a feed gas in a molar ratio of propane:ammonia:air = 1:1.2:15. The results are shown in Table 5.

EXAMPLE 34

A solid catalyst was prepared in the same manner as in Example 33 except that the amount of the tetravalent antimony oxide ($Sb_2O_4$) in Example 33 was changed to 0.15 g, and the reaction was conducted under the same conditions as in Example 33. The results are shown in Table 5.

EXAMPLE 35

A solid catalyst was prepared in the same manner as in Example 34 except that the calcination after the addition of the tetravalent antimony oxide in Example 34 was conducted under a nitrogen stream at 550° C. for two hours, and the reaction was conducted under the same conditions as in Example 33. The results are shown in Table 5.

EXAMPLE 36

30 g of the same complex oxide as in Example 33 was pulverized in an agate mortar, and 3 g of an aqueous ammonium antimony tartarate solution (corresponding to 10% by weight of $Sb_2O_3$) was added and mixed thereto. The solid of this mixture was molded into a tablet of 5 mm in diameter and 3 mm in length by a tabletting machine, followed by pulverization and sieving to obtain a powder of from 16 to 28 mesh. The powder was calcined in an air stream at 300° C. for one hour and further in a nitrogen stream at 500° C. for two hours. Using the solid catalyst thus obtained, the reaction was conducted under the same conditions as in Example 33. The results are shown in Table 5.

EXAMPLE 37

Using a complex oxide comprising Mo, V, Te and Nb prepared in the same manner as in Example 33 except that antimony oxide was not added, the reaction was conducted under the same conditions as in Example 33. The results are shown in Table 5.

EXAMPLE 38

A complex oxide having the same catalyst composition as in Example 33 was prepared under a condition where tetravalent antimony oxide ($Sb_2O_4$) was present from the initial stage, as opposed to adding tetravalent antimony oxide ($Sb_2O_4$) after preparing a complex oxide having an empirical formula $Mo_1V_{0.3}Te_{0.23}Nb_{0.12}O_n$.

Namely, 15.7 g of ammonium metavanadate was dissolved in 325 ml of warm water, and 23.6 g of telluric acid and 78.9 g of ammonium paramolybdate were sequentially added to obtain a uniform aqueous solution. Further, 117.5 g of an aqueous ammonium niobium oxalate solution having a niobium concentration of 0.456 mol/kg was mixed thereto to obtain a slurry. To this slurry, 0.98 g of tetravalent antimony oxide ($Sb_2O_4$) was further added and mixed. This slurry was evaporated to dryness to obtain a solid. This solid was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

Using the solid catalyst thus obtained, the reaction was conducted under the same conditions as in Example 33. The results are shown in Table 5.

EXAMPLE 39

A complex oxide was prepared in the same manner as in Example 38 except that the calcination in a nitrogen stream in Example 38 was conducted at 500° C. for two hours, and the reaction was conducted under the same conditions as in Example 33. The results are shown in Table 5.

TABLE 5

|  | Conversion of propane (%) | Selectivity for acrylonitrile (%) | Yield of acrylonitrile (%) |
|---|---|---|---|
| Example 33 | 91.5 | 63.7 | 58.3 |
| Example 34 | 89.3 | 63.4 | 56.7 |
| Example 35 | 86.5 | 65.6 | 56.7 |
| Example 36 | 88.1 | 63.8 | 56.2 |
| Example 37 | 86.7 | 63.5 | 55.1 |
| Example 38 | 67.2 | 49.4 | 33.2 |
| Example 39 | 45.9 | 48.3 | 22.2 |

EXAMPLES 40 TO 68

Using the solid catalyst prepared in Example 33, reactions were conducted under various conditions, and the results are shown in Table 6.

EXAMPLES 69 TO 102

Using the solid catalyst prepared in Example 34, reactions were conducted under various conditions, and the results are shown in Table 7.

EXAMPLES 103 TO 109

Using the solid catalyst prepared in Example 33, reactions were conducted under various conditions, and the results are shown in Table 8.

When the Examples in Table 8 are compared with the Examples in Tables 6 and 7, it is evident that under the same reaction conditions, the selectivity and yield are higher in a case where antimony oxide was added later than in a case where antimony oxide was not added later.

TABLE 6

| Example Nos. | Space velocity ($hr^{-1}$) | Reaction temp. (°C.) | Feed gas composition (mol %) propane/ammonia/air | Conversion of propane (%) | Selectivity for acrylonitrile (%) | Yield of acrylonitrile (%) |
|---|---|---|---|---|---|---|
| 40 | 1,000 | 410 | 1/0.6/15 | 90.0 | 53.4 | 48.1 |
| 41 | 1,000 | 410 | 1/0.75/15 | 89.9 | 58.3 | 52.4 |
| 42 | 1,000 | 410 | 1/0.9/15 | 89.6 | 61.9 | 55.5 |
| 43 | 1,000 | 410 | 1/1.05/15 | 90.4 | 63.0 | 57.0 |
| 44 | 1,000 | 410 | 1/1.35/15 | 91.6 | 64.3 | 58.9 |
| 45 | 1,000 | 410 | 1/1.5/15 | 90.9 | 64.9 | 59.0 |
| 46 | 1,000 | 410 | 1/1.65/15 | 90.4 | 65.0 | 58.8 |
| 47 | 1,000 | 410 | 1/1.8/15 | 89.4 | 65.2 | 58.2 |
| 48 | 1,200 | 410 | 1/0.75/10 | 75.7 | 66.8 | 50.6 |
| 49 | 1,200 | 410 | 1/0.9/10 | 75.0 | 68.6 | 51.5 |
| 50 | 1,200 | 410 | 1/0.75/12 | 83.7 | 62.6 | 52.3 |
| 51 | 1,200 | 410 | 1/0.9/12 | 83.6 | 66.9 | 56.0 |
| 52 | 1,200 | 410 | 1/1.2/12 | 83.1 | 68.8 | 57.2 |
| 53 | 1,200 | 410 | 1/0.75/15 | 86.3 | 61.7 | 53.2 |
| 54 | 1,200 | 410 | 1/0.9/15 | 87.1 | 63.8 | 55.5 |
| 55 | 1,200 | 410 | 1/1.2/15 | 86.3 | 66.3 | 57.2 |
| 56 | 1,200 | 410 | 1/1.5/15 | 86.2 | 66.9 | 57.7 |
| 57 | 1,500 | 410 | 1/0.75/10 | 73.7 | 66.5 | 49.0 |
| 58 | 1,500 | 410 | 1/0.9/10 | 74.3 | 68.2 | 50.7 |
| 59 | 1,500 | 410 | 1/1.2/10 | 68.9 | 68.7 | 47.3 |
| 60 | 1,500 | 410 | 1/0.75/12 | 79.5 | 66.1 | 52.6 |
| 61 | 1,500 | 410 | 1/0.9/12 | 80.4 | 69.0 | 55.4 |
| 62 | 1,500 | 410 | 1/1.2/12 | 79.5 | 70.4 | 55.9 |
| 63 | 1,500 | 410 | 1/0.75/15 | 81.5 | 64.9 | 52.9 |
| 64 | 1,500 | 410 | 1/0.9/15 | 82.0 | 66.9 | 54.8 |
| 65 | 1,500 | 410 | 1/1.2/15 | 82.1 | 67.3 | 55.3 |
| 66 | 1,500 | 410 | 1/1.5/15 | 81.9 | 68.9 | 56.4 |
| 67 | 1,500 | 400 | 1/1.2/15 | 77.1 | 68.6 | 52.9 |
| 68 | 1,500 | 420 | 1/1.2/15 | 88.3 | 63.7 | 56.2 |

TABLE 7

| Example Nos. | Space velocity (hr$^{-1}$) | Reaction temp. (°C.) | Feed gas composition (mol %) propane/ammonia/air | Conversion of propane (%) | Selectivity for acrylonitrile (%) | Yield of acrylonitrile (%) |
|---|---|---|---|---|---|---|
| 69 | 1,000 | 400 | 1/0.6/15 | 89.5 | 56.9 | 51.0 |
| 70 | 1,000 | 400 | 1/0.75/15 | 89.8 | 60.9 | 54.7 |
| 71 | 1,000 | 400 | 1/0.9/15 | 89.8 | 63.2 | 56.8 |
| 72 | 1,000 | 400 | 1/1.5/15 | 88.2 | 61.9 | 54.6 |
| 73 | 1,000 | 400 | 1/0.75/15 | 77.5 | 64.2 | 49.8 |
| 74 | 1,000 | 400 | 1/0.75/12 | 87.3 | 63.7 | 55.6 |
| 75 | 1,000 | 400 | 1/0.9/12 | 87.0 | 64.9 | 56.5 |
| 76 | 1,000 | 400 | 1/1.2/12 | 83.4 | 63.5 | 52.9 |
| 77 | 1,200 | 400 | 1/0.75/10 | 77.8 | 67.1 | 52.1 |
| 78 | 1,200 | 400 | 1/0.9/10 | 76.7 | 67.7 | 51.9 |
| 79 | 1,200 | 400 | 1/0.75/12 | 83.9 | 66.2 | 55.5 |
| 80 | 1,200 | 400 | 1/0.9/12 | 83.4 | 67.6 | 56.4 |
| 81 | 1,200 | 400 | 1/1.2/12 | 82.0 | 66.7 | 54.8 |
| 82 | 1,200 | 410 | 1/0.9/12 | 87.5 | 63.3 | 55.4 |
| 83 | 1,200 | 400 | 1/0.75/15 | 85.4 | 64.5 | 55.1 |
| 84 | 1,200 | 410 | 1/0.75/15 | 90.9 | 59.6 | 54.2 |
| 85 | 1,200 | 400 | 1/0.9/15 | 85.5 | 66.8 | 57.2 |
| 86 | 1,200 | 410 | 1/0.9/15 | 90.3 | 62.6 | 56.5 |
| 87 | 1,200 | 400 | 1/1.2/15 | 86.2 | 64.5 | 55.6 |
| 88 | 1,200 | 410 | 1/1.2/15 | 91.2 | 63.5 | 57.9 |
| 89 | 1,200 | 400 | 1/1.5/15 | 84.8 | 64.1 | 54.3 |
| 90 | 1,200 | 410 | 1/1.5/15 | 91.0 | 65.5 | 59.7 |
| 91 | 1,200 | 400 | 1/1.8/15 | 89.3 | 65.0 | 58.1 |
| 92 | 1,500 | 400 | 1/0.6/10 | 75.3 | 67.5 | 50.8 |
| 93 | 1,500 | 400 | 1/0.75/10 | 75.6 | 69.0 | 52.2 |
| 94 | 1,500 | 400 | 1/0.9/10 | 73.9 | 69.4 | 51.3 |
| 95 | 1,500 | 400 | 1/0.75/12 | 78.9 | 68.3 | 53.9 |
| 96 | 1,500 | 400 | 1/0.75/12 | 78.5 | 68.9 | 54.1 |
| 97 | 1,500 | 410 | 1/0.9/12 | 83.3 | 67.5 | 56.2 |
| 98 | 1,500 | 400 | 1/1.2/12 | 77.3 | 67.3 | 52.0 |
| 99 | 1,500 | 410 | 1/0.9/15 | 86.4 | 64.8 | 55.9 |
| 100 | 1,500 | 410 | 1/1.2/15 | 87.1 | 66.6 | 58.1 |
| 101 | 1,500 | 410 | 1/1.5/15 | 86.2 | 67.1 | 57.8 |
| 102 | 1,500 | 410 | 1/1.8/15 | 85.4 | 66.8 | 57.1 |

TABLE 8

| Example Nos. | Space velocity (hr$^{-1}$) | Reaction temp. (°C.) | Feed gas composition (mol %) propane/ammonia/air | Conversion of propane (%) | Selectivity for acrylonitrile (%) | Yield of acrylonitrile (%) |
|---|---|---|---|---|---|---|
| 103 | 1,000 | 410 | 1/0.6/15 | 83.0 | 56.8 | 47.1 |
| 104 | 1,000 | 410 | 1/0.75/15 | 82.3 | 61.4 | 50.5 |
| 105 | 1,000 | 410 | 1/0.9/15 | 82.8 | 64.2 | 53.1 |
| 106 | 1,000 | 410 | 1/1.5/15 | 82.8 | 66.2 | 54.8 |
| 107 | 1,000 | 410 | 1/1.8/15 | 80.6 | 63.6 | 51.3 |
| 108 | 1,200 | 410 | 1/0.75/10 | 73.8 | 65.3 | 48.2 |
| 109 | 1,500 | 410 | 1/0.75/10 | 73.8 | 65.3 | 48.2 |

EXAMPLES 110 TO 114

A complex oxide having an empirical formula $Mo_1V_{0.4}Te_{0.2}Nb_{0.1}O_n$ was prepared as follows.

In 117 ml of warm water, 4.21 g of ammonium metavanadate was dissolved, and 4.13 g of telluric acid and 15.9 g of ammonium paramolybdate were sequentially added thereto to obtain a uniform aqueous solution. Further, 21.9 g of an aqueous ammonium niobium oxalate solution having a niobium concentration of 0.41 mol/kg was mixed thereto to obtain a slurry. This slurry was evaporated to dryness to obtain a solid. This solid was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

The powder X-ray diffraction of the complex oxide thus obtained was measured (using Cu-Kα-rays), whereby main diffraction peaks at diffraction angles of 2θ (°) of 22.1 (100), 28.2 (79.5), 36.2 (21.0), 45.2 (10.9) and 50.0 (12.3) were observed (the numerical values in the brackets represent relative peak intensities based on the peak at 22.1° being 100).

Then, 10 g of the complex oxide was pulverized in a mortar, and 0.1 of trivalent antimony oxide ($Sb_2O_3$) was further added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

0.5 ml of the solid catalyst thus obtained was charged into a reactor, and reactions were conducted under various conditions. The results are shown in Table 9.

COMPARATIVE EXAMPLES 115 TO 118

Using a complex oxide comprising Mo, V, Te and Nb prepared in the same manner as in Example 110 except that antimony oxide was not incorporated, reactions were conducted under various conditions, and the results are shown in Table 9.

Even when the reaction temperature was raised to be higher by 10° C. than Example 115 to increase the conversion of propane, the yield and selectivity are higher when antimony oxide was added, as is evident from the comparison of Examples having the same feed gas composition.

Using the catalyst thus obtained, the reaction was conducted under the conditions as identified in Table 10. The results are shown in the same Table.

EXAMPLE 124

A complex oxide was prepared in the same manner as in Example 123 except that the calcination in a nitrogen stream in Example 123 was conducted at 500° C. for

TABLE 9

| Example Nos. | Space velocity (hr$^{-1}$) | Reaction temp. (°C.) | Feed gas composition (mol %) propane/ ammonia/air | Conversion of propane (%) | Selectivity for acrylonitrile (%) | Yield of acrylonitrile (%) |
|---|---|---|---|---|---|---|
| 110 | 1,000 | 420 | 1/1.2/15 | 89.3 | 60.1 | 53.7 |
| 111 | 1,000 | 420 | 1/0.6/15 | 90.1 | 50.7 | 45.7 |
| 112 | 1,000 | 420 | 1/0.75/15 | 90.4 | 55.7 | 50.4 |
| 113 | 1,000 | 420 | 1/0.9/15 | 90.4 | 58.2 | 52.7 |
| 114 | 1,000 | 420 | 1/1.5/15 | 87.9 | 59.8 | 52.6 |
| 115 | 1,000 | 430 | 1/0.6/15 | 88.2 | 47.0 | 41.5 |
| 116 | 1,000 | 430 | 1/0.9/15 | 88.5 | 56.0 | 49.5 |
| 117 | 1,000 | 430 | 1/1.2/15 | 88.2 | 58.5 | 51.6 |
| 118 | 1,000 | 430 | 1/1.5/15 | 86.5 | 59.0 | 51.0 |

EXAMPLES 119 to 122

A catalyst was prepared in the same manner as in Example 110 except that tetravalent antimony oxide ($Sb_2O_4$) was used for the addition of antimony oxide to the complex oxide comprising Mo, V, Te and Nb in Example 110, and reactions were conducted under various conditions. The results are shown in Table 10.

two hours, and the reaction was conducted under the conditions as identified in Table 10. The results are also shown in the same Table.

TABLE 10

| Example Nos. | Space velocity (hr$^{-1}$) | Reaction temp. (°C.) | Feed gas composition (mol %) propane/ ammonia/air | Conversion of propane (%) | Selectivity for acrylonitrile (%) | Yield of acrylonitrile (%) |
|---|---|---|---|---|---|---|
| 119 | 1,000 | 420 | 1/0.6/15 | 89.8 | 51.3 | 46.1 |
| 120 | 1,000 | 420 | 1/0.75/15 | 90.2 | 57.0 | 51.5 |
| 121 | 1,000 | 420 | 1/0.9/15 | 90.0 | 59.2 | 53.3 |
| 122 | 1,000 | 420 | 1/1.2/15 | 89.4 | 59.1 | 52.8 |
| 123 | 1,000 | 430 | 1/1.2/15 | 74.3 | 59.5 | 44.2 |
| 124 | 1,000 | 410 | 1/1.2/15 | 41.6 | 39.6 | 16.5 |

EXAMPLE 123

A complex oxide having the same catalyst composition as in Example 110 was prepared under such a condition that tetravalent antimony oxide ($Sb_2O_4$) was present from the initial stage as opposed to adding tetravalent antimony oxide ($Sb_2O_4$) after the preparation of the complex oxide having an empirical formula $Mo_1V_{0.4}Te_{0.2}Nb_{0.1}O_n$.

Namely, in 117 ml of warm water, 4.21 g of ammonium metavanadate was dissolved, and 4.13 g of telluric acid and 15.9 g of ammonium paramolybdate were sequentially added thereto to obtain a uniform aqueous solution. Further, 21.9 g of an aqueous ammonium niobium oxalate solution having a niobium concentration of 0.41 mol/kg was added thereto to obtain a slurry. Further, to this slurry, 0.2 g of tetravalent antimony oxide ($Sb_2O_4$) was added and mixed. This slurry was evaporated to dryness to to obtain a solid. This solid was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

EXAMPLE 125

30 g of the complex oxide having an empirical formula $Mo_1V_{0.3}Te_{0.23}Nb_{0.12}O_n$ prepared as described in Example 33, was pulverized, and 0.3 g of orthoboric acid ($H_3BO_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

0.5 ml of the solid catalyst thus obtained was charged into a reactor, and a gas phase catalytic reaction was conducted at a reaction temperature of 410° C. and a space velocity SV of 1,000 hr$^{-1}$ by supplying a feed gas in a molar ratio of propane:ammonia:air=1:1.2:15. The results are shown in Table 11.

EXAMPLE 126

30 g of the complex oxide having an empirical formula $Mo_1V_{0.2}Te_{0.23}Nb_{0.12}$ prepared as described in Example 33, was pulverized, and 0.6 g of orthoboric acid ($H_3BO_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained was charged into a reactor, and a gas phase catalytic oxidation reaction of propane was conducted under the same reaction conditions as in Example 125. The results are shown in Table 11.

EXAMPLE 127

30 g of the complex oxide having an empirical formula $Mo_1V_{0.3}Te_{0.23}Nb_{0.12}$ prepared as described in Example 33, was pulverized, and 0.9 g of orthoboric acid ($H_3BO_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained was charged into a reactor, and a gas phase catalytic oxidation reaction of propane was conducted under the same reaction conditions as in Example 125. The results are shown in Table 11.

TABLE 11

|  | Conversion of propane (%) | Selectivity for acrylonitrile (%) | Yield of acrylonitrile (%) |
|---|---|---|---|
| Example 125 | 89.0 | 63.2 | 56.2 |
| Example 126 | 91.6 | 63.3 | 58.0 |
| Example 127 | 87.9 | 65.5 | 57.6 |

EXAMPLE 128

30 g of the complex oxide having an empirical formula $Mo_1V_{0.2}Te_{0.23}Nb_{0.12}$ prepared as described in Example 33, was pulverized, and 0.3 g of bismuth oxide ($Bi_2O_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained was charged into a reactor, and a gas phase catalytic reaction was conducted at a reaction temperature of 410° C. and a space velocity SV of 1,000 $hr^{-1}$ by supplying a feed gas in a molar ratio of propane:ammonia:air = 1:1.2:15. The results are shown in Table 12.

EXAMPLE 129

30 g of the complex oxide having an empirical formula $Mo_1V_{0.3}Te_{0.23}Nb_{0.12}$ prepared as described in Example 33, was pulverized, and 0.6 g of bismuth oxide ($Bi_2O_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained was charged into a reactor, and a gas phase oxidation reaction of propane was conducted under the same reaction conditions as in Example 128. The results are shown in Table 12.

EXAMPLE 130

A solid catalyst was prepared in the same manner as in Example 129 except that the temperature for calcination in a nitrogen stream after the addition of bismuth oxide in Example 129 was changed to 800° C., and a gas phase catalytic oxidation reaction of propane was conducted in the same manner as in Example 129. the results are shown in Table 12.

EXAMPLE 131

30 g of the complex oxide having an empirical formula $Mo_1V_{0.3}Te_{0.23}Nb_{0.12}$ prepared as described in Example 33, was pulverized, and 0.9 g of bismuth oxide ($Bi_2O_3$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained was charged into a reactor, and a gas phase catalytic oxidation reaction of propane was conducted under the same reaction conditions as in Example 128. The results are shown in Table 12.

EXAMPLE 132

0.5 ml of the solid catalyst prepared as described in Example 128 was charged into a reactor, and a gas phase catalytic reaction was conducted at a reaction temperature of 400° C. and at a space velocity SV of 1,000 $hr^{-1}$, by supplying a feed gas in a molar ratio of propane:ammonia:air = 1:0.75:15. The results are shown in Table 12.

EXAMPLES 133 TO 140

Using the solid catalyst prepared by the method as described in Example 129, gas phase catalytic oxidation reactions of propane were conducted under various reaction conditions. The results are shown in Table 12.

TABLE 12

| Example Nos. | Space velocity ($hr^{-1}$) | Reaction temp. (°C.) | Feed gas composition (mol %) propane/ammonia/air | Conversion of propane (%) | Selectivity for acrylonitrile (%) | Yield of acrylonitrile (%) |
|---|---|---|---|---|---|---|
| 128 | 1,000 | 410 | 1/1.2/15 | 96.4 | 58.5 | 56.4 |
| 129 | 1,000 | 410 | 1/1.2/15 | 93.5 | 60.3 | 56.3 |
| 130 | 1,000 | 410 | 1/1.2/15 | 83.2 | 67.5 | 56.2 |
| 131 | 1,000 | 410 | 1/1.2/15 | 90.0 | 63.6 | 57.3 |
| 132 | 1,000 | 400 | 1/0.75/15 | 96.5 | 55.2 | 53.3 |
| 133 | 1,500 | 410 | 1/0.75/12 | 83.9 | 66.9 | 56.2 |
| 134 | 1,500 | 420 | 1/0.75/12 | 87.8 | 64.9 | 57.0 |
| 135 | 1,500 | 410 | 1/0.9/12 | 84.0 | 66.8 | 56.1 |
| 136 | 1,500 | 420 | 1/0.9/12 | 88.2 | 66.0 | 58.2 |
| 137 | 1,500 | 410 | 1/0.75/15 | 85.8 | 65.8 | 56.5 |
| 138 | 1,500 | 420 | 1/0.75/15 | 90.4 | 62.7 | 58.7 |
| 139 | 1,500 | 410 | 1/0.9/15 | 85.1 | 66.8 | 56.9 |

TABLE 12-continued

| Example Nos. | Space velocity (hr$^{-1}$) | Reaction temp. (°C.) | Feed gas composition (mol %) propane/ammonia/air | Conversion of propane (%) | Selectivity for acrylonitrile (%) | Yield of acrylonitrile (%) |
|---|---|---|---|---|---|---|
| 140 | 1,500 | 420 | 1/0.9/15 | 90.4 | 63.6 | 57.5 |

EXAMPLE 141

30 g of the composite oxide having an empirical formula $Mo_1V_{0.3}Te_{0.23}Nb_{0.12}$ prepared as described in Example 33, was pulverized, and 0.3 g of cerium oxide ($CeO_2$) was added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 600° C. for two hours.

0.5 ml of the solid catalyst thus obtained was charged into a reactor, and a gas phase catalytic reaction was conducted at a reaction temperature of 142° C. and at a space velocity SV of 1,000 hr$^{-1}$ by supplying a feed gas in a molar ratio of propane:ammonia:air = 1:1.2:15. The results are shown in Table 13.

EXAMPLE 142

0.5 ml of the solid catalyst prepared as described in Example 141 was charged into a reactor, and a gas phase catalytic reaction was conducted at a reaction temperature of 430° C. and at a space velocity SV of 1,500 hr$^{-1}$ by supplying a feed gas in a molar ratio of propane:ammonia:air = 1:1.2:15. The results are shown in Table 13.

EXAMPLE 143

A solid catalyst was prepared in the same manner as in Example 141 except that the amount of cerium oxide in Example 141 was changed to 0.6 g. 0.5 ml of the solid catalyst thus prepared was charged into a reactor, and a gas phase catalytic reaction was conducted at a reaction temperature of 430° C. and at a space velocity SV of 1,000 hr$^{-1}$ by supplying a feed gas in a molar ratio of propane:ammonia:air = 1:1.2:15. The results are shown in Table 13.

EXAMPLE 144

0.5 ml of the solid catalyst prepared as described in Example 143 was charged into a reactor, and a gas phase reaction was conducted at a reaction temperature of 440° C. and at a space velocity SV of 1,500 hr$^{-1}$ by supplying a feed gas in a molar ratio of propane:ammonia:air = 1:1.2:15. The results are shown in Table 13.

COMPARATIVE EXAMPLES 145 to 147

Using a complex oxide comprising Mo, V, Te and Nb prepared in the same manner as in Examples 141 to 143 except that cerium oxide was not added, a gas phase catalytic oxidation reaction of propane was conducted under the same conditions as in Examples 141 to 143. The results are shown in Table 13.

TABLE 13

| Example Nos. | Space velocity (hr$^{-1}$) | Reaction temp. (°C.) | Conversion of propane (%) | Selectivity for acrylonitrile (%) | Yield of acrylonitrile (%) |
|---|---|---|---|---|---|
| 141 | 1,000 | 420 | 93.2 | 58.4 | 54.7 |

TABLE 13-continued

| Example Nos. | Space velocity (hr$^{-1}$) | Reaction temp. (°C.) | Conversion of propane (%) | Selectivity for acrylonitrile (%) | Yield of acrylonitrile (%) |
|---|---|---|---|---|---|
| 142 | 1,500 | 430 | 87.5 | 64.9 | 56.8 |
| 143 | 1,000 | 430 | 91.8 | 57.1 | 52.4 |
| 144 | 1,500 | 440 | 88.9 | 61.2 | 54.4 |
| 145 | 1,000 | 420 | 94.2 | 56.7 | 53.4 |
| 146 | 1,500 | 430 | 94.2 | 57.2 | 53.8 |
| 147 | 1,000 | 430 | 91.3 | 53.8 | 49.2 |

EXAMPLE 148

30 g of the complex oxide having an empirical formula $Mo_1V_{0.3}Te_{0.23}Nb_{0.12}$ prepared as described in Example 33, was pulverized, and 0.225 g of tetravalent antimony oxide ($Sb_2O_4$) and 0.6 g of bismuth oxide ($Bi_2O_3$) were added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained, was charged into a reactor, and a gas phase reaction was conducted at a reaction temperature of 410° C. and a space velocity SV of 1,000 hr$^{-1}$ by supplying a feed gas in a molar ratio of propane:ammonia:air = 1:1.2:15. The results are shown in Table 14.

EXAMPLE 149

30 g of the complex oxide having an empirical formula $Mo_1V_{0.3}Te_{0.23}Nb_{0.12}$ prepared as described in Example 33, was pulverized, and 0.1125 g of tetravalent antimony oxide ($Sb_2O_4$) and 0.3 g of bismuth oxide ($Bi_2O_3$) were added and mixed thereto. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours.

0.5 ml of the solid catalyst thus obtained, was charged into a reactor, and a gas phase reaction was conducted at a reaction temperature of 400° C. and a space velocity SV of 1,000 hr$^{-1}$ by supplying a feed gas in a molar ratio of propane:ammonia:air = 1:1.2:15. The results are shown in Table 14.

EXAMPLE 150

0.5 ml of the solid catalyst prepared as described in Example 149 was charged into a reactor, and a gas phase catalytic reaction was conducted at a reaction temperature of 410° C. and at a space velocity SV of 1,500 hr$^{-1}$ by supplying a feed gas in a molar ratio of propane:ammonia:air = 1:1.2:15. The results are shown in Table 14.

EXAMPLE 151

To 5 ml of water, 0.277 g of bismuth nitrate pentahydrate ($Bi(NO_3)_3 \cdot 5H_2O$) was added, and 0.167 g of tetravalent antimony oxide ($Sb_2O_4$) was further added. The mixture was evaporated to dryness. The solid thus obtained was calcined in an air stream at 600° C. for two hours.

To the solid thus obtained, 30 g of the composite oxide having an empirical formula $Mo_1V_{0.3}Te_{0.23}Nb_{0.1}2O_n$ prepared as described in Example 33, was added and mixed. This mixture was molded into a tablet of 5 mm in diameter and 3 mm in length by a tabletting machine, followed by pulverization and sieving to obtain a powder of from 16 to 28 mesh. The powder was calcined in a nitrogen stream at 550° C. for two hours. Here, the atomic ratio of Sb:Bi was 2:1.

0.5 ml of a solid catalyst thus obtained, was charged into a reactor, and a gas phase catalytic reaction was conducted at a reaction temperature of 410° C. and a space velocity SV of 1,000 hr$^{-1}$ by supplying a feed gas in a molar ratio of propane:ammonia:air = 1:1.2:15. The results are shown in Table 14.

EXAMPLE 152

0.5 ml of a solid catalyst prepared as described in Example 150, was charged into a reactor, and a gas phase catalytic reaction was conducted at a reaction temperature of 410° C. and at a space velocity SV of 1,500 hr$^{-1}$ by supplying a feed gas in a molar ratio of propane:ammonia:air = 1:1.2:15. The results are shown in Table 14.

TABLE 14

| Example Nos. | Space velocity (hr$^{-1}$) | Reaction temp. (°C.) | Conversion of propane (%) | Selectivity for acrylonitrile (%) | Yield of acrylonitrile (%) |
|---|---|---|---|---|---|
| 150 | 1.000 | 410 | 90.1 | 64.0 | 57.6 |
| 151 | 1.000 | 400 | 94.5 | 59.0 | 55.8 |
| 152 | 1.500 | 410 | 90.5 | 63.7 | 57.7 |
| 153 | 1.000 | 410 | 94.8 | 61.1 | 57.9 |
| 154 | 1.500 | 410 | 89.0 | 64.7 | 57.6 |

EXAMPLE 155

30 g of the composite oxide having an empirical formula $Mo_1V_{0.3}Te_{0.23}Nb_{0.12}O_n$ prepared as described in Example 33, was pulverized, and 0.225 g of tetravalent antimony oxide ($Sb_2O_4$) was added and mixed thereto. This mixture was molded into a tablet of 5 mm in diameter and 3 mm in length by a tabletting machine, followed by pulverization and sieving to obtain a product of from 16 to 28 mesh. The powder was calcined in a nitrogen stream at 550° C. for two hours. 0.5 ml of a solid catalyst thus obtained was charged into a reactor, and a gas phase catalytic reaction was conducted at a reaction temperature of 420° C. and at a space velocity SV of 1,000 hr$^{-1}$ by supplying a feed gas in a molar ratio of isobutane:ammonia:air = 1:1.2:15.

As a result, the conversion of isobutane was 61.4%, the selectivity for methacrylonitrile was 33.0, and the yield of methacrylonitrile was 20.3%.

EXAMPLE 156

Using a complex oxide comprising Mo, V, Te and Nb prepared in the same manner as in Example 155 except that antimony oxide was not added, a gas phase catalytic oxidation reaction of isobutane was conducted under the same conditions as in Example 155.

As a result, the conversion of isobutane was 64.1%, the selectivity for methacrylonitrile was 29.7%, and the yield of methacrylonitrile was 18.1%.

EXAMPLE 157

A material having silica incorporated in an amount of 10% by weight, based on the total amount, to a complex oxide having an empirical formula $Mo_1V_{0.3}Te_{0.23}Nb_{0.1}2O_n$, was prepared as follows.

In 117 ml of warm water, 3.79 g of ammonium metavanadate was dissolved, and 3.72 g of telluric acid and 14.30 g of ammonium paramolybdate were sequentially added thereto to obtain a uniform aqueous solution. Further, 3.59 g of ammonium niobium oxalate dissolved in 17.9 ml of water and 10.24 g of silica sol (silica content: 20% by weight) were added thereto to obtain a slurry. This slurry was evaporated to dryness at 150° C. to obtain a dried product.

This dried product was molded into a tablet of 5 mm in diameter and 3 mm in length by a tabletting machine, followed by pulverization and sieving to obtain a powder of from 16 to 28 mesh. The powder was calcined in a nitrogen stream at a temperature of 600° C. for 4 hours.

The powder X-ray diffraction of the complex oxide thus obtained, was measured, whereby main diffraction peaks were observed at diffraction angles of $2\theta$ (°) of 22.1 (100), 28.2 (41.7), 36.2 (10.0), 45.2 (13.1) and 50.1 (7.1) (the numerical values in the brackets indicate the relative peak intensities based on peak at 22.1° being 100).

0.5 ml of the material thus obtained was charged into a reactor, and a gas phase catalytic oxidation reaction was conducted at a reaction temperature of 420° C. and a space velocity SV of 1,000 hr$^{-1}$ by supplying a feed gas in a molar ratio of propane:ammonia:air = 1:1.2:15. As a result, the conversion of propane was 88.9%, the selectivity for acrylonitrile was 60.5%, and the yield of acrylonitrile was 53.8%.

EXAMPLE 158

A gas phase catalytic oxidation reaction of isobutane was conducted in the same manner as in Example 157 except that the complex oxide of Example 3 was used.

As a result, the conversion of isobutane was 52.1%, the selectivity for methacrylonitrile was 31.0%, and the yield of methacrylonitrile was 16.2%.

COMPARATIVE EXAMPLE 7

A gas phase catalytic oxidation reaction of isobutane was conducted in the same manner as in Example 157 except that the complex oxide of Comparative Example 2 was used.

As a result, the conversion of isobutane was 11.0%, the selectivity for methacrylonitrile was 42.7%, and the yield of methacrylonitrile was 4.7%.

According to the process of the present invention, it is possible to produce a desired nitrile at a relatively low temperature at a level of from 400° to 450° C. in good yield without necessity of the presence of a halide or water in the reaction system, by using a novel complex oxide catalyst and an alkane as the starting material.

We claim:

1. A process for preparing an $\alpha,\beta$-ethylenically unsaturated nitrile, which comprises subjecting an alkane of 3 to 7 carbon atoms and ammonia in the gaseous state to catalytic oxidation in the presence of a catalyst under a stream of molecular oxygen gas at an elevated vapor phase temperature and at a pressure and for a time sufficient to prepare said α,β-ethylenically unsaturated nitrile, which catalyst satisfies the following conditions (1) and (2):

(1) the catalyst is represented by the empirical formula (I):

$$Mo_aB_bTe_cX_xO_n \qquad (I)$$

wherein X is at least one element selected from the group consisting of Nb, Ta, W, Ti Al, Zr, Cr, Mn, Fe, Ru, Co, Rh, Ni, Pd, Pt, Sb, Bi, B and Ce, and wherein a is 1, b is 0.01 to 1.0, c is 0.01 to 1.0, and x is 0.01 to 1.0, and n is a number such that the total valency of the metal elements is satisfied; and (2) the catalyst has X-ray diffraction peaks at the following angles of 2θ in its X-ray diffraction pattern:

| Diffraction angles of 2θ (°) |
| --- |
| 22.1 ± 0.3 |
| 28.2 ± 0.3 |
| 36.2 ± 0.3 |
| 45.2 ± 0.3 |
| 50.0 ± 0.3 |

2. The process according to claim 1, wherein in the formula (1), when a is 1, b is 0.1 to 0.6, c is 0.05 to 0.4 and x is 0.01 to 0.6.

3. The process according to claim 1, wherein in the formula (1), X is Nb.

4. The process according to claim 1, wherein the X-ray diffraction peaks in the X-ray diffraction pattern of the catalyst have the following characteristics:

| Diffraction angles of 2θ (°) | Relative intensity |
| --- | --- |
| 22.1 ± 0.3 | 100 |
| 28.2 ± 0.3 | 20 to 150 |
| 36.2 ± 0.3 | 5 to 60 |
| 45.2 ± 0.3 | 2 to 40 |
| 50.0 ± 0.3 | 2 to 40 |

5. The process according to claim 1, wherein the catalyst is prepared by drying an aqueous solution containing compounds of molybdenum, vanadium and tellurium and a compound of at least one element selected from the group consisting of Nb, Ta, W, Ti, Al, Zr, Cr, Mn, Fe, Ru, Co, Rh, Ni, Pd, Pt, Sb, Bi, B and Ce; calcining the dried product in the absence of oxygen to obtain a complex oxide; adding to the complex oxide an oxide containing at least one element selected from the group consisting of Sb, Bi, Ce, and B; and calcining the mixture.

6. The process according to claim 1, wherein the catalyst is prepared by drying an aqueous solution containing compounds of molybdenum, vanadium, and tellurium and a compound of at least one element selected from the group consisting of Nb, Ta, W, Ti, Al, Zr, Cr, Mn, Fe, Ru, Co, Rh, Ni, Pd, Pt, Sb, Bi, B and Ce; calcining the dry product in the absence of oxygen to obtain a complex oxide; adding to the complex oxide an organic compound containing at least one element selected from the group consisting of Sb, Bi, Ce, and B; and calcining the mixture.

7. The process according to claim 1, wherein the alkane is propane.

8. The process according to claim 1, wherein the ammonium is reacted in an amount of from 0.2 to 5 moles per mole of alkane.

9. A process for preparing an α,β-ethylenically unsaturated nitrile, which comprises subjecting an alkane of 3 to 7 carbon atoms and ammonia in the gaseous state to catalytic oxidation in the presence of a catalyst under a stream of molecular oxygen gas at an elevated vapor phase temperature and at a pressure and for a time sufficient to prepare said α, β-ethylenically unsaturated nitrile, said catalyst being obtained by drying an aqueous solution containing compounds of molybdenum, vanadium and tellurium and a compound of at least one element selected from the group consisting of Nb, Ta, W, Ti, Al, Zr, Cr, Mn, Fe, Ru, Co, Rh, Ni, Pd, Pt, Sb, Bi, B and Ce, and calcining the dried product in the absence of oxygen, wherein the catalyst is represented by the empirical formula (I):

$$Mo_aB_bTe_cX_xO_n \qquad (I)$$

wherein X is at least one element selected from the group consisting of Nb, Ta, W, Ti, Al, Zr, Cr, Mn, Fe, Ru, Co, Rh, Ni, Pd, Pt, Sb, Bi, B and Ce, and wherein a is 1, b is 0.01 to 1.0, c is 0.01 to 1.0, and x is 0.01 to 1.0, and n is a number such that the total valency of the metal elements is satisfied; and wherein the catalyst has X-ray diffraction peaks at the following angles of 2θ in its X-ray diffraction pattern:

| Diffraction angles of 2θ (°) |
| --- |
| 22.1 ± 0.3 |
| 28.2 ± 0.3 |
| 36.2 ± 0.3 |
| 45.2 ± 0.3 |
| 50.0 ± 0.3 |

10. The process according to claim 9, wherein the calcination is conducted at a temperature of 350° to 700° C.

11. The process of claim 9, which further comprises after calcining the dried product in the absence of oxygen, adding to the complex oxide thereof an oxide containing at least one element selected from the group consisting of Sb, Bi, Ce and B, and calcining the mixture.

12. The process of claim 9, which further comprises after calcining the dried product in the absence of oxygen to obtain a complex oxide, adding to the complex oxide an organic compound containing at least one element selected from the group consisting of Sb, Bi, Ce and B, prior to calcining the mixture.

* * * * *

UNITED STATES PATENT AND TRADEMARK OFFICE
CERTIFICATE OF CORRECTION

PATENT NO. : 5,281,745
DATED : JANUARY 25, 1994
INVENTOR(S) : TAKASHI USHIKUBO ET AL

It is certified that error appears in the above-indentified patent and that said Letters Patent is hereby corrected as shown below:

Column 25, line 10, "$Mo_aB_bTe_cX_xO_n$" should read --$Mo_aV_bTe_cX_xO_n$--.

Column 26, line 28, "$Mo_aB_bTe_cX_xO_n$" should read --$Mo_aV_bTe_cX_xO_n$--.

Signed and Sealed this

Fourteenth Day of March, 1995

*Attest:*

BRUCE LEHMAN

*Attesting Officer*     *Commissioner of Patents and Trademarks*